United States Patent [19]

Katoh et al.

[11] Patent Number: 4,491,592
[45] Date of Patent: Jan. 1, 1985

[54] METHOD FOR TREATMENT OF INFLAMMATION

[75] Inventors: Yoshinori Katoh, Misato; Tetsuya Tajima, Nagareyama; Isao Yamatsu; Takeshi Suzuki, both of Ushikumachi; Shinya Abe, Kukizakimura; Akiharu Kajihara, Yatabemachi; Tohru Sugitani, Abiko, all of Japan

[73] Assignee: Eisai Co., Ltd., Tokyo, Japan

[21] Appl. No.: 543,184

[22] Filed: Oct. 18, 1983

[30] Foreign Application Priority Data

Oct. 21, 1982 [JP] Japan ................. 57-183641

[51] Int. Cl.³ ............................................. A61K 31/20
[52] U.S. Cl. ................................................. 424/318
[58] Field of Search ......................... 424/318

[56] References Cited

U.S. PATENT DOCUMENTS 4,346,109  8/1982  Yamatsu .......................... 424/318

Primary Examiner—Stanley J. Friedman
Attorney, Agent, or Firm—Flynn, Thiel, Boutell & Tanis

[57] ABSTRACT

A method for treatment of inflammation is disclosed which utilizes 3,7,11,15-tetramethyl-2,4,6,10,14-hexadecapentaenoic acid represented by the following chemical structural formula:

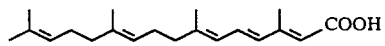

or a salt thereof, as the active ingredient.

9 Claims, No Drawings

METHOD FOR TREATMENT OF INFLAMMATION

This invention relates to a method for treating inflammation. More particularly, this invention relates to such a method using an anti-inflammatory agent comprising 3,7,11,15-tetramethyl-2,4,6,10,14-hexadecapentaenoic acid represented by the following chemical structural formula (I):

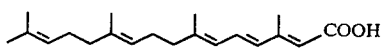 (I)

or a salt thereof, as the active ingredient.

The compound (I) has been previously found to be effective as an anticancer drug and as a therapeutic agent for treatment of skin diseases accompanied by hyperkeratosis, as disclosed in Japanese patent application No. 44558/1980 (Japanese Patent Laid-Open No. 140946/1981), which corresponds to U.S. patent application Ser. No. 249,245, filed Mar. 30, 1981, and Japanese patent application No. 104420/1980 (Japanese Patent Laid-Open No. 31615/1982), which corresponds to U.S. Pat. No. 4,346,109. The entire contents of U.S. patent application Ser. No. 249,245, filed Mar. 30, 1981, are incorporated herein by reference. The latter application describes processes for preparing all-trans-3,7,11,15-tetramethyl-2,4,6,10,14-hexadecapentaenoic acid-1 and the utility thereof for the treatment of skin diseases with keratinization, allergic and inflammatory skin diseases, reduction of the size of papillomata and for treatment of cancer. The entire contents of U.S. Pat. No. 4,346,109 are also incorporated herein by reference.

Since these previous inventions, the present inventors have investigated other effects of the compound (I) and, as a result, have unexpectedly found that this compound is also extremely effective as an anti-inflammatory agent for treating arthritic and rheumatic disorders.

At present, steroid hormones, nonsteroidal drugs, anti-inflammatory enzyme preparations (immunosuppressive agents) and the like are used as anti-inflammatory agents for treatment of joint inflammation resulting from arthritis and related conditions. Nonsteroidal drugs are typified by indoleacetic acid type compounds such as indomethacin, phenylacetic acid type compounds such as ibufenac and ibuprofen, salicylic acid type compounds such as aspirin, salicylic acid and salicylsalicylic acid, anthranilic acid type compounds such as mefenamic acid and flufenamic acid, pyrazolidinedione type compounds such as phenylbutazone, hydroxyphenylbutazone and ketophenylbutazone, and basic drugs such as benzydamine, mepirizole and tinoridine. However, these nonsteroidal drugs clinically cause severe side effects such as gastrointestinal and kidney problems.

Indomethacin, for example, which is a typical member of the group of indoleacetic acid type compounds that are considered to have the strongest anti-inflammatory action among the commercially available nonsteroidal anti-inflammatory drugs, is also considered to be the best therapeutic agent for treatment of rheumatism among nonsteroidal anti-inflammatory drugs. Indomethacin has a potent therapeutic anti-inflammatory effect, but it also has side effects such as serious gastrointestinal reactions, central nervous system reactions and kidney reactions, which are serious obstacles to the effective use of it. These side effects become a particularly serious problem in the treatment of diseases such as rheumatism, because prolonged continuous administration of large dosages of the anti-inflammatory drug are needed for effective treatment of this disease. Various different drugs are used to treat rheumatism, because the effects and side effects of such anti-inflammatory drugs differ greatly with individual patients. Accordingly, there is a world-wide demand for the development of new anti-inflammatory drugs which are long-acting and low in side effects.

The compound of the present invention is different from the above-mentioned nonsteroidal drugs and has not previously been used for the treatment of arthritic and rheumatic disorders. In addition, the compound of the present invention is a drug having an extremely low toxicity and high safety and, therefore, it has an extremely high value as a new type of nonsteroidal anti-inflammatory drug. Accordingly, it is an object of this invention to provide a new method for the treatment of arthritic and rheumatic disorders, particularly joint inflammation associated with rheumatism and arthritis, and arthritic edema.

The compound used in the method of the invention is 3,7,11,15-tetramethyl-2,4,6,10,14-hexadecapentaenoic acid represented by the following chemical structural formula:

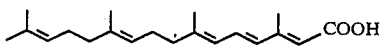 (I)

or a pharmacologically acceptable salt thereof, preferably the sodium and potassium salts thereof.

The compound (I) can be prepared, for example, by the following methods.

Method A (i) A compound represented by the general formula (II):

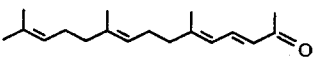 (II)

is reacted with a Wittig reagent derived from a compound represented by the general formula (III):

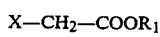 (III)

$X-CH_2-COOR_1$ wherein X is a halogen and $R_1$ is a lower alkyl group, to obtain a compound represented by the general formula (IV):

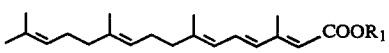 (IV)

wherein $R_1$ is as defined above, and (ii) the compound of the general formula (IV) is hydrolyzed in the presence of a base to obtain the compound of general formula (I).

As the Wittig reagents derived from a compound of the general formula (III) in the above step (i), phosphorus compounds obtained by reacting a compound of the general formula (III) with triphenylphosphine, phenyldialkoxyphosphine, trialkyl phosphite or the like can be used. Preparation of this reagent and the Wittig reaction step (i) can be carried out by ordinary methods, for example, by the method of Wadworth et al, *J. Am.*

Chem. Soc., Vol. 80, p. 1733 (1961), the method of Greenwald et al, J. Org. Chem., Vol. 28, p. 1128 (1963), or the method of Horner et al, Ber., Vol. 95, p. 581 (1962).

In the above step (ii), hydrolysis can be carried out using a base such as sodium hydroxide or potassium hydroxide normally used in the hydrolysis of carboxylate esters.

Method B (i) A compound represented by the general formula (V):

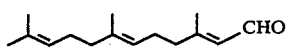
(V)

is reacted with a Wittig reagent derived from a compound represented by the general formula (VI):

(VI)

wherein X is a halogen and $R_1$ is a lower alkyl group, to obtain the compound of the general formula (IV) as shown above, and (ii) the compound of the general formula (IV) is hydrolyzed in the presence of a base to obtain the compound of the general formula (I).

The steps (i) and (ii) of Method B can be carried out in the same manner as described for Method A.

Method C (i) A compound represented by the general formula (VII):

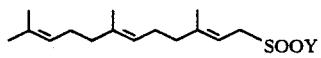
(VII)

wherein Y denotes a lower alkyl or an aryl group, is reacted with a compound of the general formula (VI) to obtain a compound represented by the general formula (VIII):

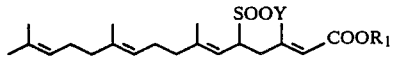
(VIII)

wherein $R_1$ and Y are as defined above, and (ii) the compound of the general formula (VIII) is desulfinated and hydrolyzed in the presence of a base to obtain the compound of the general formula (I).

The step (i) of Method C is carried out in the presence of a base such as n-butyllithium or phenyllithium. Tetrahydrofuran, diethyl ether, 1,2-dimethoxyethane or a like organic liquid is used as the reaction medium. The reaction is usually carried out at below room temperature.

Examples of the substituents X, $R_1$ and Y in the compounds of the above general formulas (III), (IV), (VI), (VII) and (VIII) are as follows. X includes halogen atoms such as chlorine, bromine or iodine. $R_1$ includes lower alkyl groups such as methyl, ethyl or propyl, and Y includes alkyl groups such as methyl, ethyl or propyl, and aryl groups such as phenyl or p-tolyl.

In order to demonstrate the effects of this invention in more detail, the results of a pharmacological experiment using the compound of the present invention are given in the following Experimental Example.

EXPERIMENTAL EXAMPLE

Suppressive effect of the compound (I) on adjuvant arthritis (1) Experimental procedures Six week-old F-344 rats (produced by Nippon Charles River) were used. Adjuvant arthritis was developed in these rats according to the method described in Winder, C. V., et al, Arthritis Rheu., Vol. 12, pp. 472–482 (1969), and the arthritis suppressing action of the compound (I) was measured. Adjuvant arthritis was developed in the rats by injecting 0.05 ml of a fluid paraffin suspension containing Mycobacterium butyricum (Difco.) in an amount of 6 mg/ml into the sole of the right hind foot of each rat. The compound (I) was administered in the form of a suspension in peanut oil. The administration was started two days before inoculation of the adjuvant and continued for seven consecutive days after the inoculation. The adjuvant arthritis lesion was comprehensively measured in terms of volume changes in the adjuvant-treated limb and the opposite (untreated) limb, the weights of organs (suprarenal gland, thymus and spleen), overall weight gain, and A/G ratio.

Expansion of the foot sole of the rats was measured five times, namely, before adjuvant inoculation and 3, 7, 14 and 21 days after the inoculation, three times in case of the opposite limb, by a mercurial pressure transduction method in which each sole was submerged in water to a marked depth and the intensity of edema was calculated according to the following formula:

$$\text{intensity of edema} = \frac{\text{volume of limb after treatment}}{\text{volume of limb before treatment}}$$

All verifications of experimental significance were made according to the t-verification method.

(2) Experimental results (1) Intensity of edema

Table 1 shows the influence of the compound (I) on the intensity of edema caused by adjuvant arthritis.

TABLE 1

| Treatment | Dosage (mg/kg) *1 | Dosage Treated limb after 3 days | after 7 days | after 14 days | after 21 days | Opposite limb after 14 days | after 21 days |
|---|---|---|---|---|---|---|---|
| Control | — | 1.34 ± 0.05 | 1.17 ± 0.10 | 1.21 ± 0.12 | 1.65 ± 0.19 | 0.17 ± 0.03 | 0.56 ± 0.09 |
| Present invention compound | 100 | 1.43 ± 0.11 | 1.10 ± 0.10 | 0.99 ± 0.13 | 1.27 ± 0.21 | 0.25 ± 0.06 | 0.67 ± 0.03 |
|  | 200 | 1.18 ± 0.06 | 0.98 ± 0.05 | 0.78 ± 07** | 0.92 ± 0.14** | 0.12 ± 0.03 | 0.22 ± 0.06** |

**There is a significant difference between the administered and the control groups at a 1% level.
*1 — based on the body weight of the rats As is apparent from Table 1, the compound (I) began to exhibit its adjuvant arthritis suppressing effect seven days after the start of administration and, in the group given the 200 mg/kg dosage, exhibited highly significant adjuvant arthritis suppression 14 days and 21 days after the start of administration.

(2) Influence of compound (I) on weight of organs and total body weight.

Table 2 shows the changes in body weight and the changes in weights of organs which were removed after the final measurements in the course of the Experimental Example.

TABLE 2

| Treatment | Dosage (mg/kg) | Suprarenal Gland | Thymus | Spleen | Initial weight | Final weight | Weight gain |
|---|---|---|---|---|---|---|---|
| Control | — | 49.8 ± 1.6 | 126 ± 7 | 866 ± 31 | 122 ± 2 | 145 ± 2 | 23 |
| Present invention compound | 100 | 46.0 ± 3.6 | 148 ± 24 | 825 ± 65 | 120 ± 1 | 156 ± 8 | 36 |
| | 200 | 40.9 ± 2.9* | 207 ± 22** | 749 ± 109 | 122 ± 2 | 178 ± 8** | 56 |

*There is a significant difference between the administered and the control groups at a 5% level.
**There is a significant difference between the administered and the control groups at a 1% level.

In the adjuvant arthritis rats tested, hypertrophy of the suprarenal gland due to stress and hyperfunction of the suprarenal gland occurred, resulting in atrophy of the thymus. Further, a marked expansion of the spleen also occurred. As is apparent from Table 2, improvement in the weights of the suprarenal gland, thymus and spleen as well as the remission of overall weight gain inhibition were recognized in the group given the 200 mg/kg dosage of the compound (I) of the present invention.

(3) A/G ratio

Table 3 shows the influence of the test on the serum protein of the adjuvant arthritis rats.

TABLE 3

| Treatment | Dosage (mg/kg) | Total protein | Albumin | A/G ratio |
|---|---|---|---|---|
| Control | — | 7.10 ± 0.14 | 3.76 ± 0.06 | 1.14 ± 0.03 |
| Present invention compound | 100 | 6.93 ± 0.34 | 3.81 ± 0.15 | 1.26 ± 0.07 |
| | 200 | 6.58 ± 0.20 | 3.84 ± 0.05 | 1.46 ± 0.11* |

*There is a significant difference between the administered and the control groups at a 5% level.

The A/G (albumin/globulin) ratio serves as a parameter for measuring general symptoms of adjuvant arthritis. In the adjuvant arthritis rats, the A/G ratio is reduced from values of 1.6 to 2.0 for normal healthy rats. This is considered to be associated with an increase in serum globulin and a decrease in serum albumin. As is apparent from Table 3, the compound (I) ameliorates the decrease in the A/G ratio, that is, lessens the difference between the A/G values for normal rats and the A/G values for rats treated so as to have adjuvant arthritis.

The results of a test of the toxicity of the compound (I) of the present invention are given below.

Toxicity test

The compound (I), 3,7,11,15-tetramethyl-2,4,6,10,14-hexadecapentaenoic acid, was orally administered to groups of 6 ICR strain mice (female) in dosages of 40, 200, or 400 mg/kg/day for 14 consecutive days, and changes in weight, occurrence of death and the like were observed. There were no cases where death occurred, and side effects such as weight loss and cyanosis were not observed.

From the results of the above pharmacological experiment and the toxicity test, it was determined that the compound (I) is useful as a highly safe and excellent anti-inflammatory and antirheumatic agent. Accordingly, the compound (I) can be used continuously for a long period as an anti-inflammatory agent or an antirheumatic agent, and in this respect the value of this invention is particularly high.

When used as an anti-inflammatory/antirheumatic drug in the treatment of human beings or animals, the compound (I) or a pharmacologically acceptable salt thereof is administered orally or parenterally, for example, intramuscularly, subcutaneously, intravenously, or as a suppository. Although the dosage to be administered depends on the condition and age of the subject and is difficult to generally specify, it is usually about 0.1 to 2,000 mg/adult/day, preferably about 0.1 to 500 mg/adult/day, particularly 0.1 to 400 mg/adult/day.

The compound (I) is incorporated into a suitable dosage form, such as tablets, granules, a powder, capsules, an injectable liquid preparation or a suppository by conventional methods of drug preparation. To obtain an orally administrable solid preparation, the compound of the present invention is mixed with an excipient and, if necessary, also with a binder, a disintegrator, a lubricant, a coloring agent and a corrigent, and then is formed by a conventional method into tablets, coated tablets, granules, powder, capsules or the like.

As excipients, there are used, for example, lactose, cornstarch, sucrose, glucose, sorbitol, crystalline cellulose and silicon dioxide. As binders, for example, polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone, sucrose and sorbitol are used. As disintegrators, for example, starch, agar, gelatin powder, crystalline cellulose, calcium carbonate, sodium hydrogencarbonate, calcium citrate, dextrin and pectin are used. As lubricants, for example, magnesium stearate, talc, polyethylene glycol, silica and hydrogenated vegetable oils are used. As coloring agents, any of those which are acceptable as additives for pharmaceuticals can be employed. As corrigents, cocoa powder, menthol, aromatic powder, peppermint oil, borneol, cinnamon powder and the like can be employed. The tablets or granules can be sugar-coated, gelatin-coated or otherwise coated using conventional methods and coating materials.

The liquid preparation for oral administration is prepared by mixing the compound (I) with a corrigent, a buffering agent, a stabilizer, and optionally other conventionally employed additives, and the mixture is then made into a syrup.

To prepare an injectable liquid, the compound of the invention is mixed with a pH modifier, a buffering agent, a suspending agent, a dissolution aid, a stabilizer, an isotonizing agent, a preservative, and other conventional additives, and is then made into a hypodermic, intramuscular or intravenous injection liquid by well-known methods.

As suspending agents, mention can be made of, for example, methylcellulose, Polysolvate 80, hydroxyethylcellulose, gum arabic, tragacanth powder, sodium carboxymethylcellulose and polyoxyethylene sorbitan monolaurate. As dissolution aids, polyoxyethylene hydrogenated castor oil, Polysolvate 80, nicotinamide, polyoxyethylene sorbitan monolaurate, macrogol, castor oil fatty acid ethyl ester and the like can be employed. As stabilizers, for example, sodium bisulfite, sodium metabisulfite and ether can be used, and as preservatives, methyl p-hydroxybenzoate, ethyl p-hydroxybenzoate, sorbic acid, phenol, cresol, chlorocresol and the like can be used.

An Example and a Preparative Example are given below.

PREPARATIVE EXAMPLE 1

Preparation of 3,7,11,15-tetramethyl-2,4,6,10,14-hexadecapentaenoic acid.

28.6 g of triethyl phosphonoacetate was added to a suspension of 5.0 g of 55% sodium hydride (in oil) in 60 ml of n-hexane and heated under reflux. To this solution was added dropwise with agitation 20 g of 6,10,14-trimethylpentadeca-3,5,9,13-tetraen-2-one. After 30 minutes, the reaction solution was poured onto 200 ml of ice water and extracted with 500 ml of n-hexane. The n-hexane layer was washed twice with 100 ml of a methanol/water (2:1) mixture and then concentrated. The concentrated product was purified by silica gel chromatography to obtain 18 g of an ethyl ester which was ethyl 3,7,11,15-tetramethyl-2,4,6,10,14-hexadecapentaenoate.

3.9 g of potassium hydroxide was dissolved in 30 ml of isopropyl alcohol. To this solution was added 10 g of the foregoing ethyl ester and the resulting mixture was stirred at 50° C. for one hour. The reaction solution was poured onto ice water, acidified with hydrochloric acid and extracted with 100 ml of ethyl ether. The ether layer was washed with water, dried over magnesium sulfate and condensed to obtain 9.0 g of an oil product. This product was dissolved in 50 ml of n-hexane and crystallized at −20° C. to obtain 4.0 g of 3,7,11,15-tetramethyl-2,4,6,10,14-hexadecapentaenoic acid as light yellow needlelike crystals having the following properties:

melting point: 78.4° C.

mass spectrum (m/e): 302 (M+)

infrared absorption spectrum (cm$^{-1}$, KBr tablet): 3450, 2900, 1680, 1595

NMR spectrum (δ, CDCl$_3$): 1.61 (6H, s), 1.68 (3H, s), 1.86 (3H, s), 1.92~2.24 (8H, b), 2.35 (3H, s), 5.10 (2H, b), 5.76 (1H, bs), 5.98 (1H, d, J=11 Hz), 6.20 (1H d, J=15 Hz), 6.90 (1H, dd, J=11 Hz, 15 Hz), 11.63 (1H, b)

ultraviolet absorption spectrum: $\lambda_{max}^{methanol}$ 304 nm.

EXAMPLE 1: TABLET

| | |
|---|---|
| 3,7,11,15-tetramethyl-2,4,6,10,14-hexadecapentaenoic acid | 50 g |
| silic anhydride | 30 g |
| crystalline cellulose | 50 g |
| cornstarch | 36 g |
| hydroxypropylcellulose | 10 g |
| magnesium stearate | 4 g |

Tablets (180 mg/tablet) were prepared from a mixture having the foregoing composition by a conventional method.

We claim:

1. A method of treating a subject suffering from arthritic or rheumatic disorder characterized by joint inflammation, comprising administering to said subject a therapeutically effective amount of 3,7,11,15-tetramethyl-2,4,6,10,14-hexadecapentaenoic acid of the formula:

[structural formula]COOH or a pharmaceutically acceptable salt thereof.

2. A method according to claim 1, wherein a dosage of from 0.1 mg to 2000 mg per day of said 3,7,11,15-tetramethyl-2,4,6,10,14-hexadecapentaenoic acid or pharmaceutically acceptable salt thereof is administered to an adult patient.

3. A method according to claim 1, wherein said 3,7,11,15-tetramethyl-2,4,6,10,14-hexadecapentaenoic acid or salt thereof is administered orally.

4. A method according to claim 1, wherein said 3,7,11,15-tetramethyl-2,4,6,10,14-hexadecapentaenoic acid or salt thereof is administered by injection.

5. A method according to claim 1, wherein said 3,7,11,15-tetramethyl-2,4,6,10,14-hexadecapentaenoic acid or salt thereof is administered by a suppository.

6. A method according to claim 2, wherein said dosage is from 0.1 to 500 mg per day.

7. A method according to claim 2, wherein said subject is suffering from joint inflammation due to arthritis.

8. A method according to claim 2, wherein said subject is suffering from joint inflammation due to rheumatism.

9. A method of treating a subject suffering from arthritic edema, comprising administering to said subject a therapeutically effective amount of 3,7,11,15-tetramethyl-2,4,6,10,14-hexadecapentaenoic acid of the formula:

[structural formula]COOH or a pharmaceutically acceptable salt thereof.

* * * * *